Figure 1:
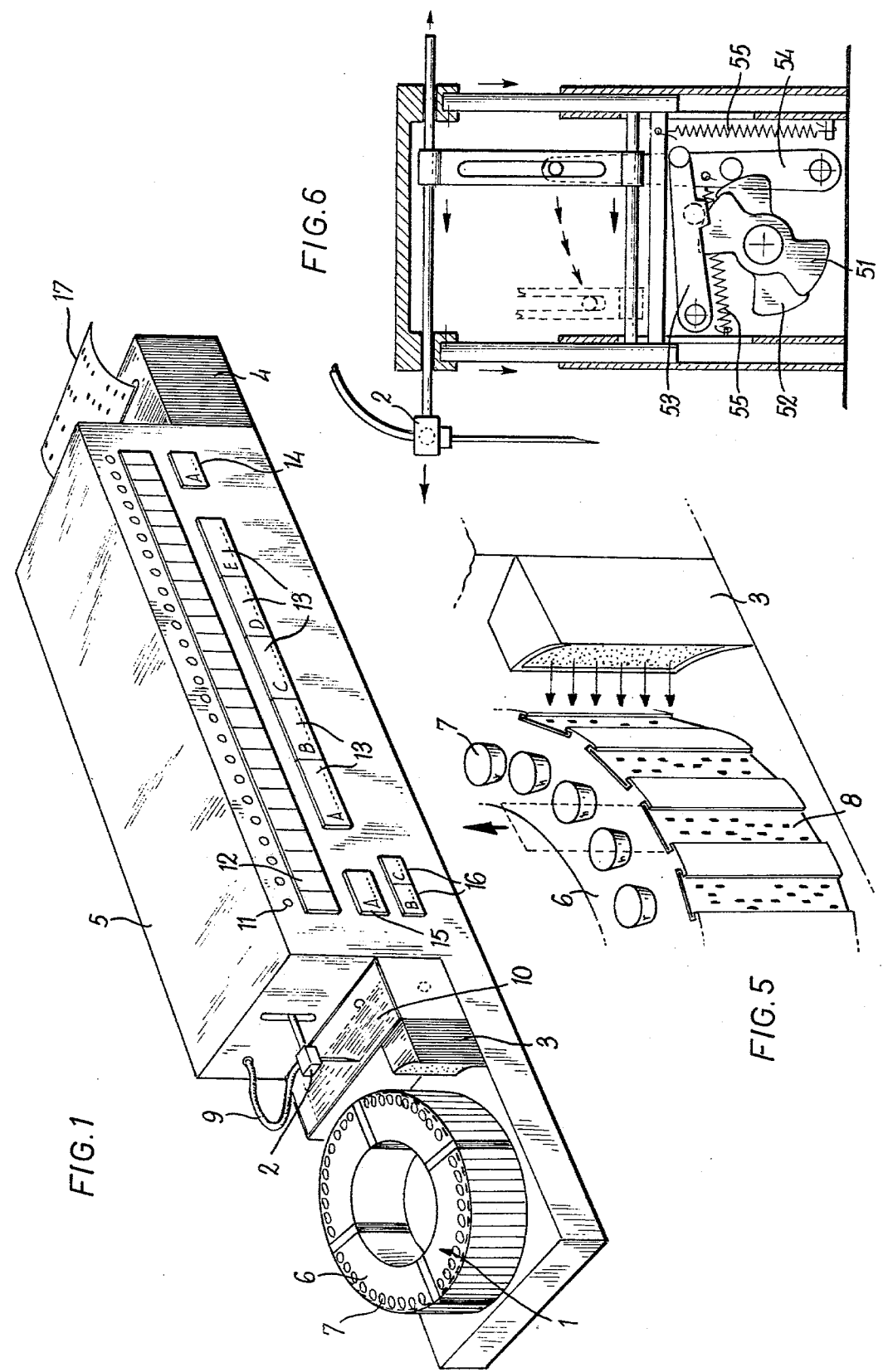

United States Patent [19]

Welch

[11] 4,259,288

[45] Mar. 31, 1981

[54] AUTOMATIC MULTICHANNEL APPARATUS FOR PERFORMING ANALYSES ON FLUIDS, IN PARTICULAR FOR PERFORMING CLINICAL-CHEMISTRY ANALYSES ON BIOLOGICAL LIQUIDS

[76] Inventor: Henry H. Welch, No. 437, Via Nomentana, Rome, Italy

[21] Appl. No.: 11,590

[22] Filed: Feb. 12, 1979

[30] Foreign Application Priority Data

Feb. 15, 1978 [IT]  Italy ............................... 48060 A/78

[51] Int. Cl.³ ........................ G01N 35/06; G01N 1/14
[52] U.S. Cl. .................................. 422/63; 73/423 A; 364/497; 364/498; 422/64; 422/67; 422/103
[58] Field of Search ..................... 422/64, 65, 67, 103, 422/63; 73/423 A; 356/39, 246; 364/497, 498

[56] References Cited

U.S. PATENT DOCUMENTS

| | | | |
|---|---|---|---|
| 3,617,222 | 11/1971 | Matte | 356/39 X |
| 3,660,638 | 5/1972 | Oberli | 422/67 X |
| 3,754,444 | 8/1973 | Ure et al. | 73/423 A |
| 3,762,879 | 10/1973 | Moran | 422/67 |
| 3,909,203 | 9/1975 | Young et al. | 422/67 |
| 3,912,456 | 10/1975 | Young | 422/64 |
| 3,917,455 | 11/1975 | Bak et al. | 422/67 |
| 4,058,367 | 11/1977 | Gilford | 422/67 |

*Primary Examiner*—R. E. Serwin
*Attorney, Agent, or Firm*—Beveridge, De Grandi, Kline & Lunsford

[57] ABSTRACT

An automatic multichannel apparatus for performing analyses on fluids, comprising, in combination, an array of sample-holder test tubes, mounted on an intermittently indexed drum, a needle for sample withdrawal carried by a mobile arm and adapted to be successively introduced into the test tubes to aspirate samples to be analyzed, a distributor-mixer complex, for distributing the sample to be analyzed on many segments and adding the various reagents for the various analyses to the samples, means for measuring photometrically the samples and printout of the data related to the analyses.

7 Claims, 12 Drawing Figures

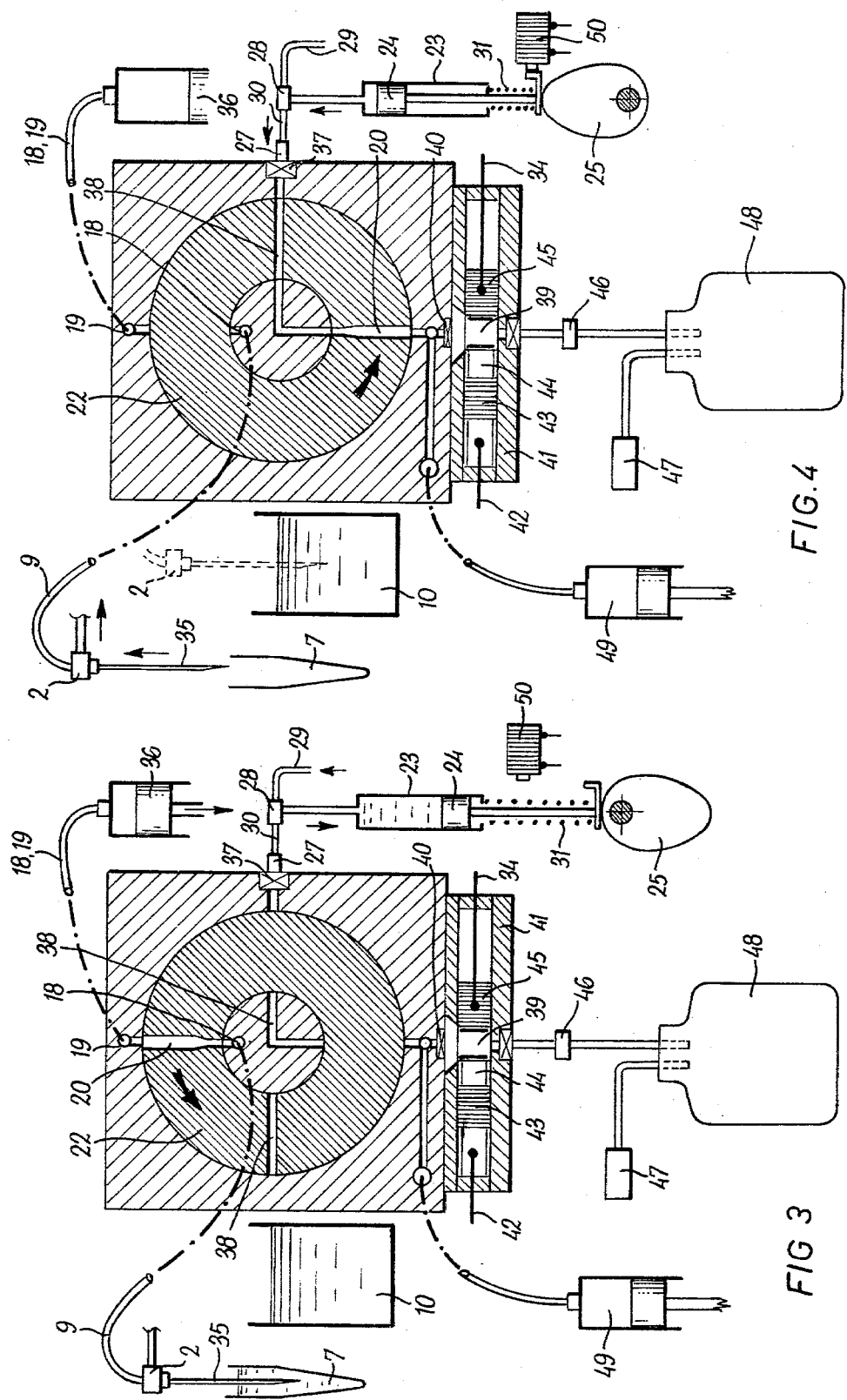

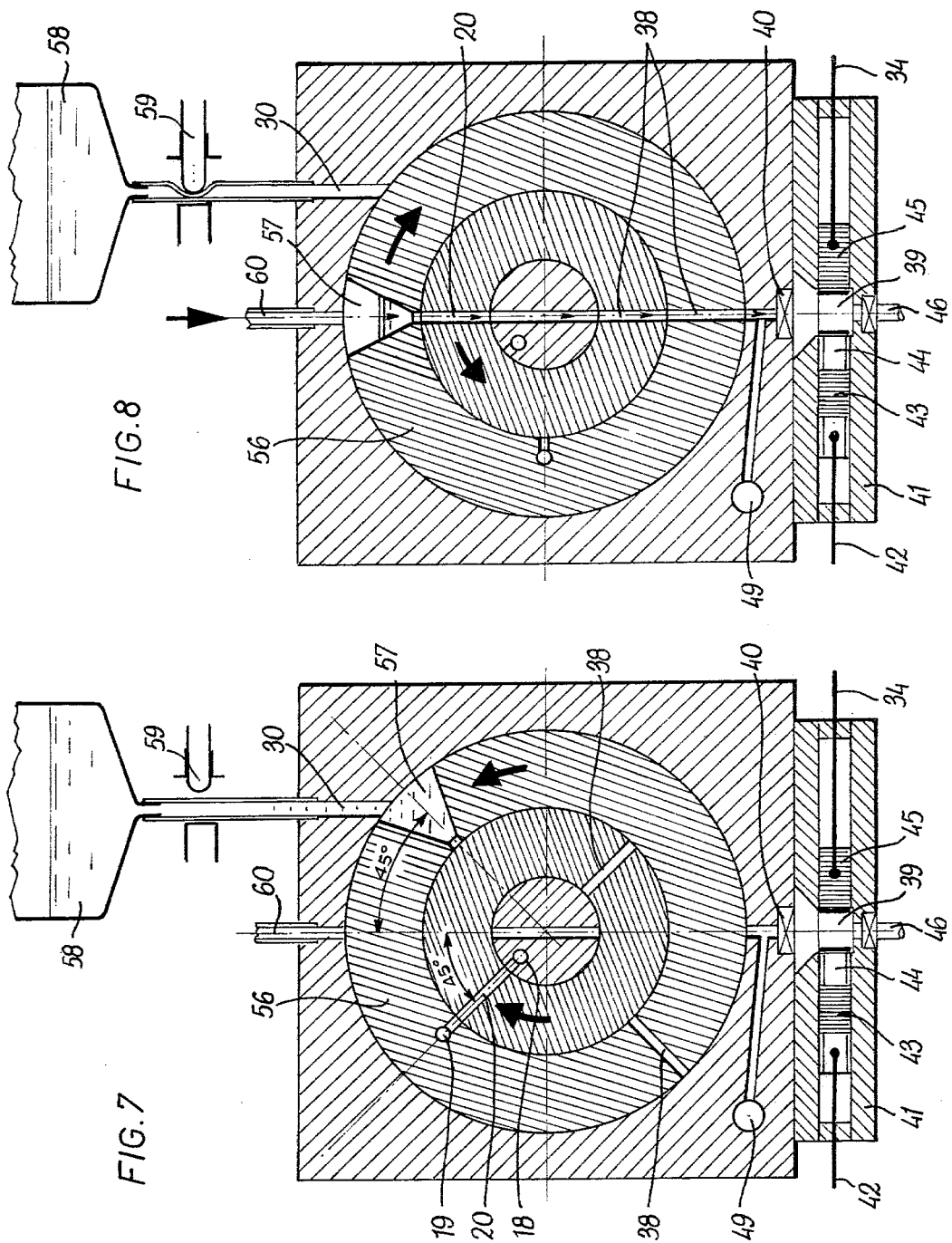

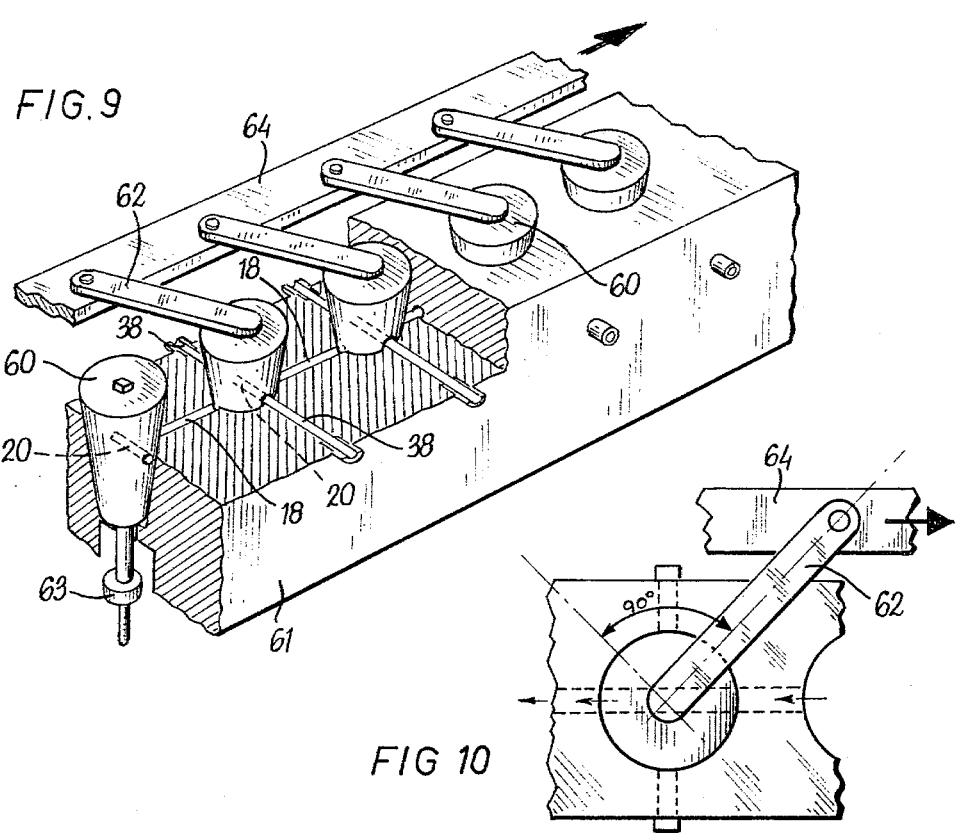
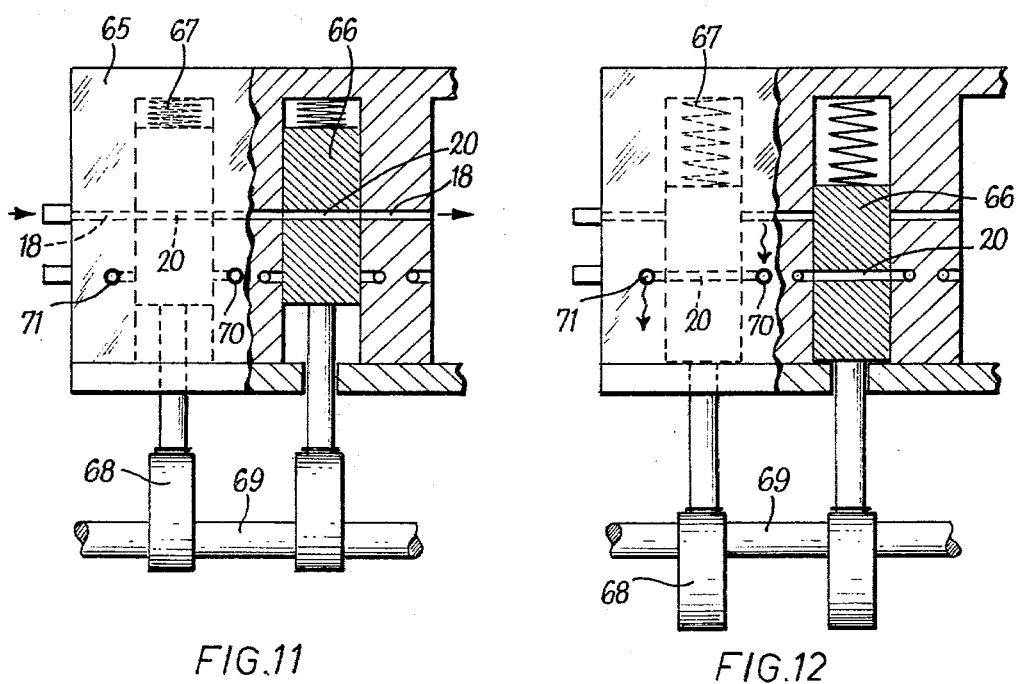

AUTOMATIC MULTICHANNEL APPARATUS FOR PERFORMING ANALYSES ON FLUIDS, IN PARTICULAR FOR PERFORMING CLINICAL-CHEMISTRY ANALYSES ON BIOLOGICAL LIQUIDS

The present invention is related to an automatic multichannel apparatus for performing analyses on fluids, in particular clinical-chemistry analyses on biological fluids.

In particular, the present invention concerns a multichannel apparatus which enables one to perform from one to thirty or more different analyses simultaneously, from a signle aspirated sample aliquot. In a specific way the present invention concerns an apparatus for performing rapidly and accurately a plurality of different analyses on a single fluid sample or groups of fluid samples.

With the development and the diffusion of preventive medicine and of greater control over hospital patients the necessity arises for performing a larger number of analyses of different types for each patient. Consequently an automatic equipment which would enable one to perform simultaneously different types of analyses on the same sample has become indispensable. Moreover, due to the great increase of data and tests required for each patient, the big problem arises of transcribing the data incoming from the different types of apparatuses or different departments or laboratories, with the possibility of human error increasing with the greater number of analyses to perform and transcribe.

The present invention provides also equipment which allows perfect identification of the sample, inclusive of the printing of the patient's case-sheet by means of a computer, with particular interfaces and programs specifically studied for this purpose.

The main object of the present invention is to provide an automatic multichannel apparatus which can perform with great precision and rapidity a wide number of analyses of different types, simultaneously, on the same sample. This system not only automates each one of the subsequent phases of the processes used in analytical and clinical chemistry but it introduces also characteristics of simplicity and of versatility which do not necessarily require specialized technicians. It eliminates the old manual methods, transcription errors, and the need of specialized technical personnel, and it offers a modern technique with more precise data and results, which are impossible to obtain with manual operation.

Another object of the invention consists in providing an automatic multichannel equipment, for fluid analyses, wherein each sample is treated discretely and independently, thus eliminating the possibility of errors or of contamination.

A further object of the present invention is to provide a multichannel system which enables one to obtain results of one to 30 or more different analyses simultaneously, within 2 to 3 minutes. This allows also for emergency use in hospital.

Another object of the present invention is to provide a system which uses microamounts of sample and microamounts of reagents in order to reduce costs.

Another object of the present invention is to provide a system which is able to perform from a single to several analyses at the same time, according to the patient's need.

According to the present invention, an apparatus is provided comprising in combination, a first sampler complex to hold a plurality of samples to be analyzed, set in a crown of four segments. Each segment holds 10 sample-containing test tubes. A sample identification card is inserted outside each test tube, and it bears the indication of the analyses to be performed on the sample itself. The identification card is read at the moment of withdrawing of the sample, and the data are transmitted to the computer and printed out together with the results on a patient data-sheet.

Said segments are interchangeable and other segments may be added as the analyses are performed.

The sample is aspirated into a segmented tube in an amount sufficient to perform all the analyses (up to thirty or more). Each segment represents an analysis. The size of the segment corresponds to the size of the sample necessary for a given test. The segment is washed with a precise amount of specific reagent into a proper thermostated cuvette where the chemical reaction and the photometric measurement occur. The data of the various measurements are transferred to the computer which processes and prints the results directly on a patient's data-sheet. After each sample, all the system is washed out before introducing the next sample in order to avoid contamination.

The present invention will now be described with reference to the attached drawings which represent, as a non limitative example, some of the preferred embodiments of the present invention itself.

Figure 2:
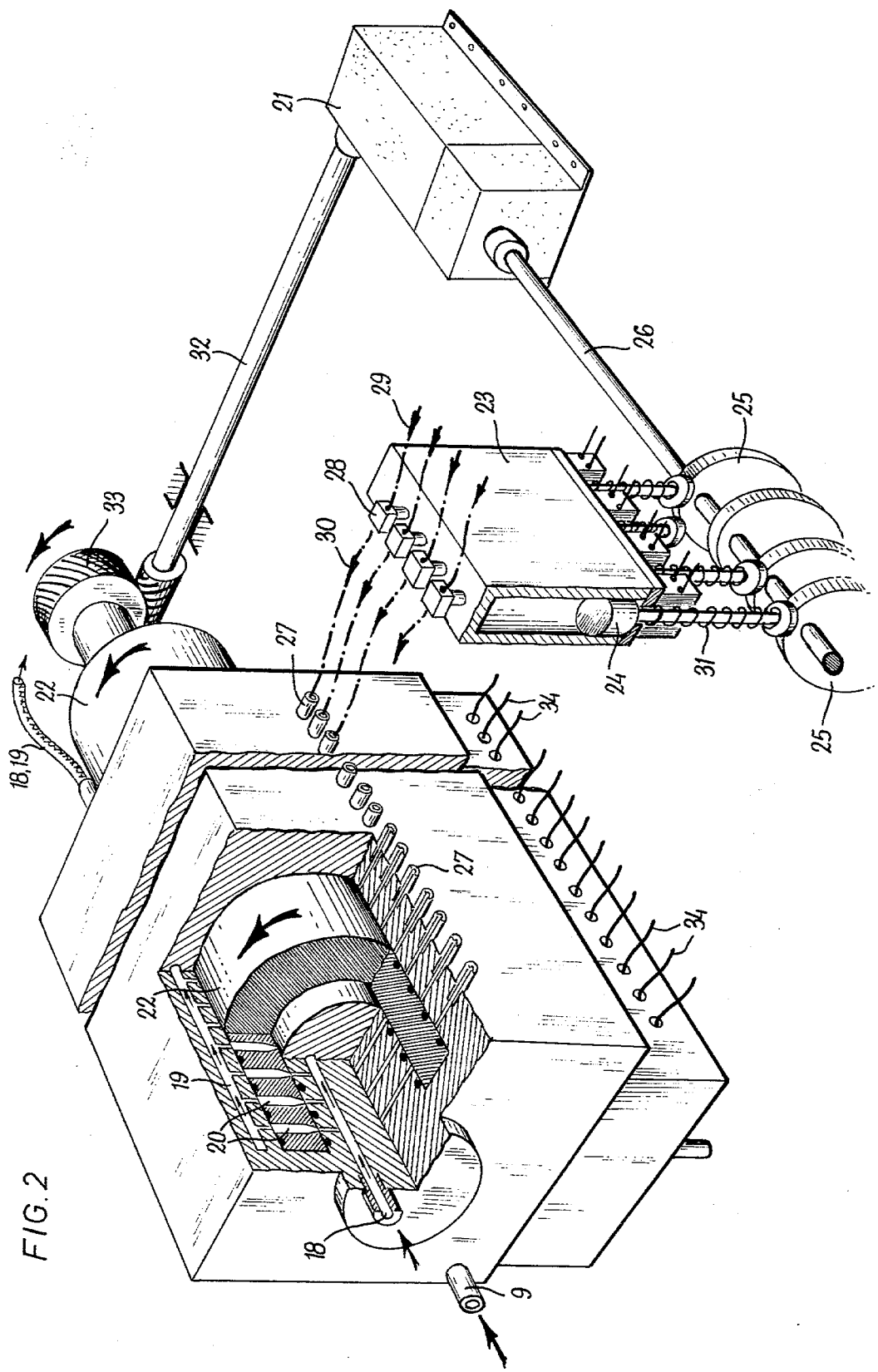

In the drawings:

FIG. 1 is a perspective view of the apparatus according to the present invention, FIG. 2 represents a partially sectioned, axonometric view, FIGS. 3 and 4 represent two cross sectional views, FIG. 5 represents the sample identification complex, FIG. 6 represents the detail of the sample withdrawal arm movement, FIGS. 7 and 8 represent the sectional view of a second type of the distributor complex, FIGS. 9 and 10 represent the sectional view of another embodiment of the distributor complex, FIGS. 11 and 12 represent a partially sectioned lateral perspective view of the reagent delivery system.

With reference to FIGS. 1 to 6, the apparatus comprises a circular plate, indicated by 1, a self-propelled arm system 2, an optical system for the identification of sample 3, a computer 4 with means for printing results and the apparatus body, 5.

Sample holder test tubes 7 are housed within circular plate 1, consisting of 4 equal seqments 6, a card 8 is inserted in front of each test tube containing information about the analyses which have to be performed on that sample, inclusive of a coded number or particular identification of the client.

Self-propelled arm 2, operated by an electrical motor and controlled by the computer enters into sample holder test tube 7 and withdraws an amount of liquid to be analyzed. The liquid is transported into tube 9 to the analytical system within apparatus body 5. After analyzing the sample, the self-propelled arm enters into container 10 containing distilled water and aspirates liquid to wash out the system to eliminate contamination between one sample and another.

Each analysis is identified by means of a pilot lamp 11, the pilot lamps 11 being identical in number to the number of analyses that the apparatus can perform simultaneously. The pilot lamps 11 light up according to the analyses which have to be performed on the sample under analysis. In the same way the computer controls the proper performance of the system, and in the event of trouble on a particular channel the respective pilot lamp 12 lights up. Pilot lamps 13 indicate the cycle of operation under way, such as sample withdrawing, reagent delivery, incubation time, sample reading and the printing of results.

Push button 14 serves to start up the apparatus. Pilot lamp 15 indicates that the apparatus is ready for the operation. Push botton 16 operates the "START" and "STOP" of the apparatus. Form 17, on which are printed the result data with their identification, is controlled by computer 4.

The aspiration system of the liquid to be examined is seen, partially sectioned, in FIG. 2. The sample, aspirated by the self-propelled arm 2 is transported through tube 9 within channels 18 and 19 which communicate with radial cavities 20 carried by distributing cylinder 22.

For each type of analysis to be performed, there exists a small channel or cavity 20. The size of a cavity 20 corresponds to the amount of liquid sample necessary to perform a given analysis. The liquid aspirated from test tube 7 is in such amount as to fill the whole of channels 18 and 19 including cavity 20. By operating motor 21, distributing cylinder 22 rotates 180°, thus causing the rotation through 180° of the cavities 20. Operated by same motor, the reagent delivery system 23 is activated to deliver the reagent. For each cavity 20 there corresponds a piston 24 which is pushed up by a cam 25 placed along axis 26 of motor 21. Each piston 24 pushes the liquid out into a passage 27, to push in turn the liquid to be analyzed into a cuvette.

A three-way reagent valve 28 makes it possible for the delivery system to operate. The various reagents to be used are aspirated by pistons 24 through tubes 29 and are expelled by the pistons themselves through tubes 30, when pistons 24 are pushed up by their respective cams 25. After delivery of the reagents the respective pistons 24 are automatically pushed down by their respective springs 31 to load new reagents to the syringes.

Motor 21 also operates shaft 32, which, through worm screw and gear wheel 33, makes cylinder 22 rotate 180°. Conductors 34 are used to transmit signals indicative of the results to the computer 4.

The whole analytical system and the related functioning can be seen, in section, in FIGS. 3 and 4. Sampling arm 2 enters into sample holding test tube 7, and through needle 35, aspirates the liquid sample to be analyzed. Said liquid is aspirated by operating microsyringe 36. The liquid sample is drawn through tube 9 and fills channels 18 and 19 and all the relative radial cavity 20. Cylinder 22 turns 180° to the delivering position seen in FIG. 4. Needle 35 comes out from sample holding test tube 7. Motor 21 is activated which, besides turning cylinder 22, moves axis 26 activating cams 25, which push pistons 24, thus delivering the reagents through valves 28.

The reagent, through tube 30, reaches opening 27. Valve 37 opens and forces the reagent through channel 38, to force the liquid to be analyzed into cavity 20 and the reagent to enter into cuvette 39 by opening a cuvette valve 40. Cuvette 39 is incorporated in a heating plate 41. Lamp 42 lets the light pass through optical system 43 and filter 44 through the cuvette containing the liquid under examination. The amount of light transmitted is measured by an electronic detector 45, and the related signal is transmitted through lead wire 34 to the electronic system for data processing.

The solution under examination remains in cuvette 39 for the time necessary to develop the reaction and perform the measurements. During the reaction and the measurement time, cylinder 22 rotates back 180° to return to the starting position.

Sampling arm 2 enters into container 10, containing distilled water, and withdraws water to wash out all the tubes and channels where the preceding sample has passed, to eliminate possible contamination from the previous sample. Thus tube 9, channels 18 and 19 and the radial cavities 20 are all washed with distilled water and air and are now ready to withdraw the next sample to be analyzed. After the sample has been measured into cuvette 39 and the results printed by the computer, vacuum valve 46 opens and withdraws the liquid under examination from cuvette 39. Vacuum pump 47 generates a vacuum in waste bottle 48 and the liquid under examination is withdrawn. Washing syringes 49, which push distilled water into cuvette 39 are activated and, after the latter has been washed, the water is withdrawn into waste bottle 48. A further vacuum suction dries cuvette 39 to prepare for the arrival of the next sample to be analyzed. Magnet 50 has the task of blocking reagent delivering piston 24 whenever necessary. Inasmuch as it is not necessary to perform all the possible analyses for each sample by the apparatus, (the non requested analyses), piston 24 is blocked when up, so that the reagent is not delivered and the analysis is not performed. In this way the reagent, often an expensive item, is not wasted.

In FIG. 5 the detail of sample holder cuvette is represented with its punched identification cards 8 and identification optical system 3 which programs the analyses to be performed on each sample.

Detail of the movement of the self-propelled arm 2 for the aspiration of the liquid to be analyzed is shown in FIG. 6. Two butterfly cams 51 and 52 operate two levers 53 and 54 which, in turn, operate arm 2 vertically and horizontally in cooperation with springs 55.

Another embodiment of the analytical delivering system and of its functioning is shown in section, in FIGS. 7 and 8. It is another embodiment of the complex illustrated in FIGS. 3 and 4.

The liquid to be analyzed is withdrawn through channels 18 and 19, filling all of cavity 20. Cylinder 22, already described with reference to FIGS. 3 and 4, is replaced with cylinder 56 which consists of three parts. While the liquid to be analyzed is withdrawn into the various cavities 20, the corresponding reagents fill the funnel-like cavities 57 of a number corresponding to the number of said cavities 20. Each funnel 57 is filled through a tube 30 with an amount of reagent equal in size to funnel 57 necessary for a given analysis. The reagents are added by gravity fall from reagent reservoir 58. A magnetic spring 59 compresses tube 30 when no reagent should pass through. When the liquid to be analyzed is withdrawn and funnels 57 are filled with their respective reagents, cylinder 56 turns 45° to find itself in the position of FIG. 8. Compressed air is supplied through connector 60, which pushes the reagent in funnel 57 and the liquid to be analyzed, contained in cavity 20, into cuvette 39, running through channels 38. The solution in cuvette 39 is measured as described above. During the reading, cylinder 56 turns back 45° to return to its initial position. Small channels 18 and 19 are washed with distilled water aspirated from container 10, as previously described, and the apparatus is ready for a subsequent sample.

Another embodiment of the analytical system and how it functions can be seen in FIGS. 9 and 10. In this case the liquid sample aspirated through needle 35 is carried into channel 18 through conical taps 60. Each cone represents one analysis. The complex is mounted on block 61 containing the desired number of cones 60, equal to the number of analyses to be performed simultaneously. A channel 18 for the sample arrival is machined out along block 61. The cones fastened within said block present small channel 20, whose volume corresponds to the amount of liquid sample necessary for a given analysis. When all cones 60 are set in such a way that their small channels are perfectly aligned with channel 18, the sample to be analyzed is drawn to fill the whole channel 18 and the various small channels 20. After aspiration of the sample, the cones are rotated 90° by means of levers 62 to put them into correspondence with channels 38 where the various reagents are brought in, to introduce the whole into cuvette 39 for the reading. Each cone 60 may be adjusted for a perfect seal by means of a screw 63. The complex of levers 62 is displaced by means of a lever 64 so that all the cones are displaced simultaneously. The lever system for the movement of cones 60 by means of levers 62 and 64 is seen in FIG. 10.

Another analytical system for the withdrawal of the liquid sample and the delivery of the reagents is seen, also sectionally, in FIGS. 11 and 12. In this case it deals with a horizontal block 65, through which channel 18 is machined out, in which the liquid to be analyzed is aspirated. Within the block there are housed small block 66. One small block 66 is inserted for each type of analysis. The size of the small block corresponds to the amount of liquid sample necessary to perform a given analysis. The liquid sample is aspirated through channel 18, also filling the small channels 20 machined out within the various small blocks 66. After the sample has been drawn in, small blocks 66 are displaced horizontally, pushed by springs 67. In order to return to their original position, the small blocks are pushed by cams 68 mounted on shaft 69 which is operated by an electric motor. The reagent is forced, in a displaced position, (FIG. 12), through hole 70, thus forcing both the reagent and the liquid sample into small channel 20 through outlet 71 inside cuvette 39 for the measurement of the sample.

It is evident, from the preceding, that the device, according to the present invention, offers the following advantages:

Possibility of subdividing the sample into several fractions (segments), exactly calibrated, to perform an extended series of analyses on the same liquid sample, which is withdrawn only once.

Each calibrated segment can be controlled with respect to the amount of liquid necessary to perform the various analyses. The volume of the various segments could be different but always in microliters.

The segmentation system for the liquid sample assures an absolute precision of the sample aspiration, which assures maximum accuracy of the analyses.

The washing system is complete and very accurate in order to eliminate contamination from one analysis to another.

By means of two simple mechanical movements it is possible to control and to perform 30 or more different analyses, simultaneously.

The cuvette is purposely built to be thermostated, and the optical system is designed in such a way as to afford the photometric measurements in kynetics, initial rate or timed reactions.

With only one power supply lamp and optical fibers, it is possible to illuminate all the various channels, in order to simplify and to assure the functioning of the reading system.

The system is completely controlled by a computer which, besides processing data on the results, controls the timing and the synchronization in the various operational phases.

Within a very few minutes it is possible to perform up to 30 or more different analyses on a liquid sample.

Single samples or large groups of samples can be analyzed with the same simplicity and only the desired analyses are performed.

The multichannel automatic apparatus can be operated by non-specialized technical personnel. It is sufficient to press a push button to obtain up to 30 or more different results on a single liquid sample.

Use of microamounts of samples and reagents with consequent cost reduction.

The present invention has been described in some preferred embodiments thereof, but it is intended that the constructional variations could be introduced in practice without departing from the protection limits of the present patent.

Having thus described the present invention, what is claimed is:

1. Automatic multichannel apparatus to perform analyses on fluids comprising in combination an intermittently indexed drum, an array of sample holder test tubes mounted on said drum, a movable arm, a needle borne by said movable arm for aspirating the sample and adapted for introduction, successively, into said test tubes, a distributor-mixer complex for distributing the sample to be analyzed in many segments and adding the various reagents for the various pre-established analyses, and means for the measuring of result data related to the analyses, said distributor-mixer complex including a fixed block, two concentric cylinders each having an annular section, sealingly mounted within said fixed block, the outer cylinder having a series of cavities having inlet ducts and adapted to be filled with the reagents and the inner cylinder having a corresponding series of radial passages adapted to be filled with the sample of liquid to be examined.

2. Apparatus according to claim 1, characterized by the fact that said sample holding test tubes are housed in said drum rotating within interchangeable sectors, and by said apparatus further comprising a plurality of cards, one card associated with each test tube, each card having coded thereon the patient's data and the tests to be performed on the sample.

3. Apparatus according to claim 2, further comprising an optical complex for reading said cards and a computer connected to said optical complex for programming the various operational phases of the distributor-mixer complex and controlling the printing of results.

4. Apparatus according to claim 1, 2, or 3 further comprising means for holding distilled water and means for causing distilled water from said holding means to pass through said needle and said cavities and passages after each cycle of analysis, to provide for each sample aspiration a washing cycle of said ducts and said cavities and passages by means of distilled water, before passing on to the next sample.

5. Apparatus according to claim 4, characterized by the fact that the washing water is withdrawn by said needle and conveyed in all the ducts, cavities and passages related both to the sample and to the reagents, said apparatus further comprising a waste vessel into which the washing water, the samples, and the reagents already used are collected.

6. Apparatus according to claim 1, 2 or 3, characterized by the fact that the feeding of the reagents is made by gravity fall, and by said apparatus further comprising a throttling valve for metering the feeding of the reagents, said throttling valve intercepting the duct of each cavity as soon as the cavity carried by the cylindrical distributor is filled.

7. Apparatus according to claim 6, further comprising means defining a reagent reservoir, a plurality of metering cuvettes, and a source of compressed air and characterized by the fact that said fixed block includes an outer part and a central core which have a series of passages communicating with the reagent reservoir, with the metering cuvettes, with the cavity ducts, and with said source of compressed air which pushes the various fractions of the sample and the associated various reagents into the metering cuvettes when the ducts and the cavities carried by the two cylinders are aligned among them, following rotation of said cylinders.

* * * * *